(12) United States Patent
Schultheiss

(10) Patent No.: US 10,201,719 B2
(45) Date of Patent: Feb. 12, 2019

(54) GANTRY SYSTEM FOR PARTICLE BEAM THERAPY

(71) Applicant: Varian Medical Systems Particle Therapy GmbH, Troisdorf (DE)

(72) Inventor: Juergen Schultheiss, Cologne (DE)

(73) Assignee: Varian Medical Systems Particle Therapy GmbH, Troisdorf (DE)

(*) Notice: Subject to any disclaimer, the term of this patent is extended or adjusted under 35 U.S.C. 154(b) by 0 days.

(21) Appl. No.: 15/474,845

(22) Filed: Mar. 30, 2017

(65) Prior Publication Data

US 2018/0280732 A1    Oct. 4, 2018

(51) Int. Cl.
*A61N 5/00* (2006.01)
*A61N 5/10* (2006.01)

(52) U.S. Cl.
CPC .... *A61N 5/1081* (2013.01); *A61N 2005/1087* (2013.01)

(58) Field of Classification Search
CPC .................. A61N 5/1081; A61N 2005/1087
USPC .................. 250/492.1, 492.2, 492.3
See application file for complete search history.

(56) References Cited

U.S. PATENT DOCUMENTS

| 8,278,633 B2 * | 10/2012 | Nord | A61N 5/1049 250/395 |
| 2012/0199760 A1 * | 8/2012 | Handa | A61N 5/1049 250/492.1 |

FOREIGN PATENT DOCUMENTS

| EP | 1738798 A2 | 1/2007 |
| EP | 2606932 A1 | 6/2013 |
| WO | 2009070173 A1 | 6/2009 |

OTHER PUBLICATIONS

European Patent Office, European Search Report in EP 18 16 4688, Aug. 28, 2018, 4 pages.

* cited by examiner

*Primary Examiner* — Nicole Ippolito
*Assistant Examiner* — Hanway Chang

(57) ABSTRACT

A particle beam delivery system includes a beam delivery line of charged particle and a gantry body supporting the beam delivery line. The gantry body is rotatably supported by a first support and a second support. The gantry body serves to rotate the beam delivery line about a horizontal axis passing through the first and second supports. The gantry body comprises a cantilevered portion configured to support at least a section of the beam delivery line in a cantilevered manner extended beyond the first and second supports. The second support is supported by a structure which is rotatable about a vertical axis passing through the second support, thereby providing clearance for the cantilevered portion of the gantry body when rotating about the horizontal axis. The gantry body may be rotatable about the horizontal axis in 360 degrees, clockwise and/or counter-clockwise. A gantry assembly and a particle beam radiotherapy system comprising a gantry assembly are also provided.

26 Claims, 7 Drawing Sheets

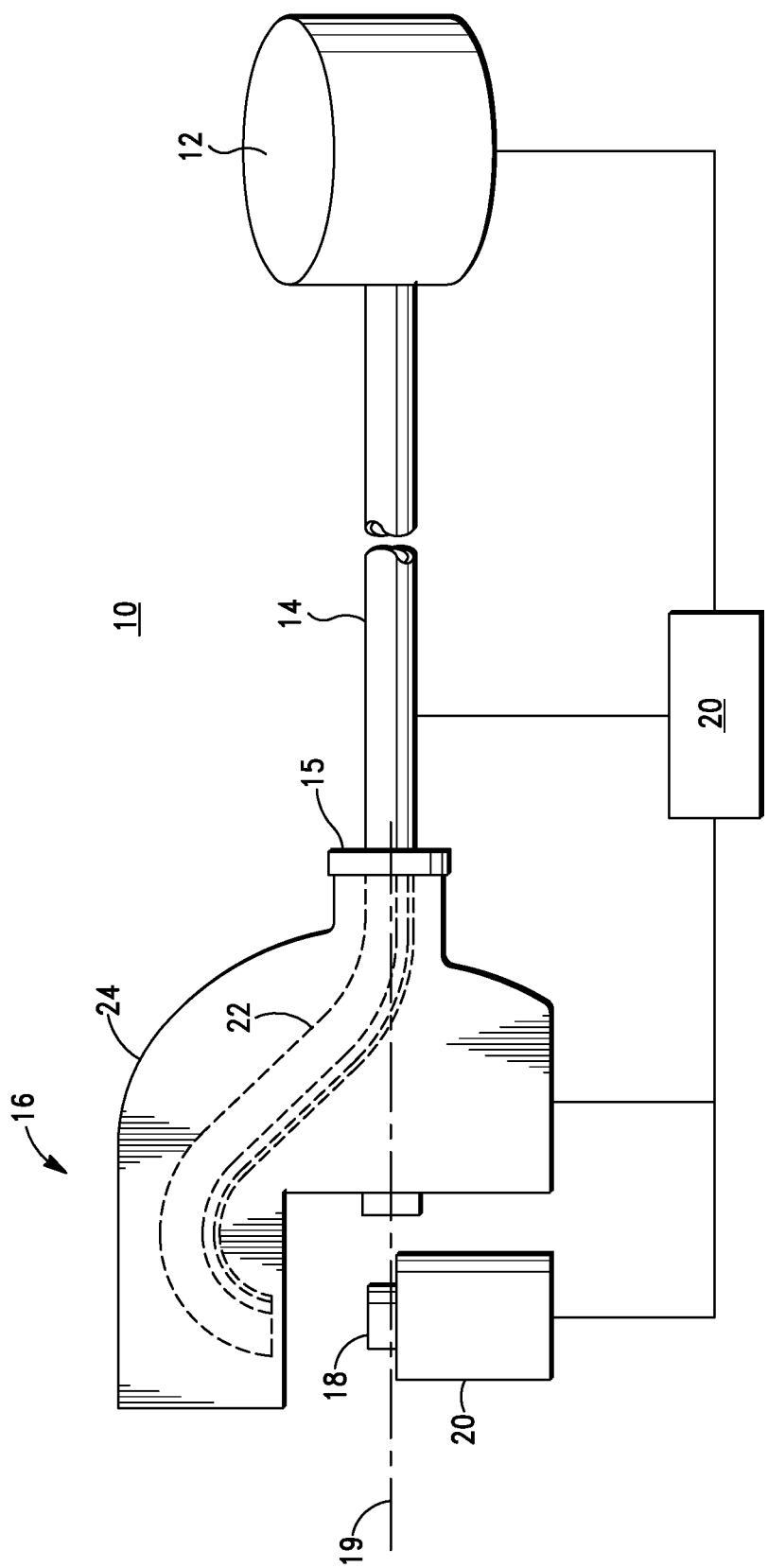

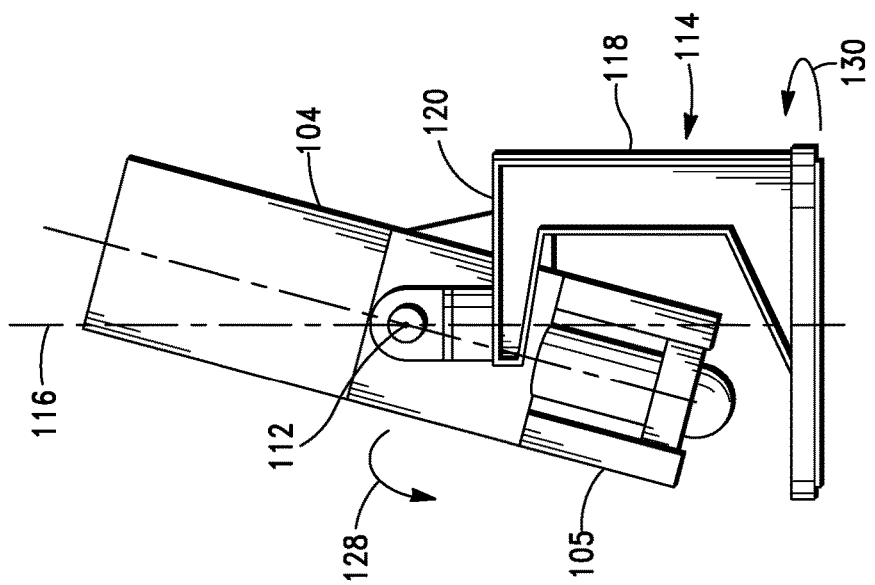
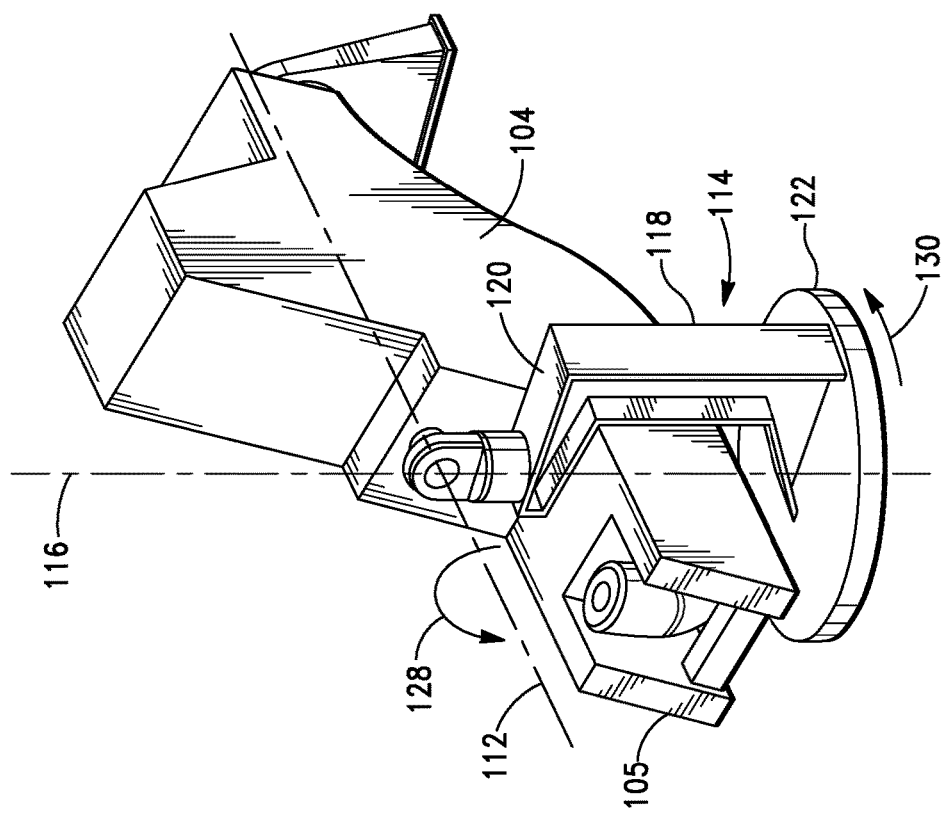
FIG. 4B
FIG. 4A

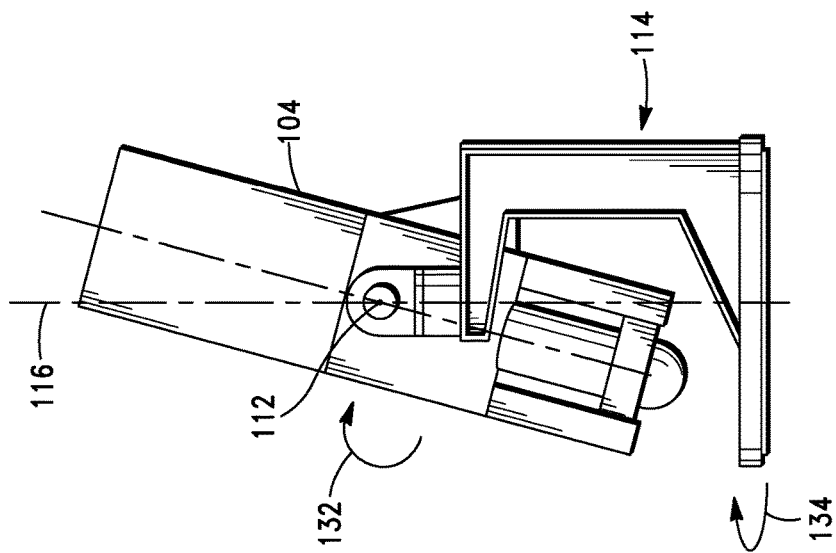
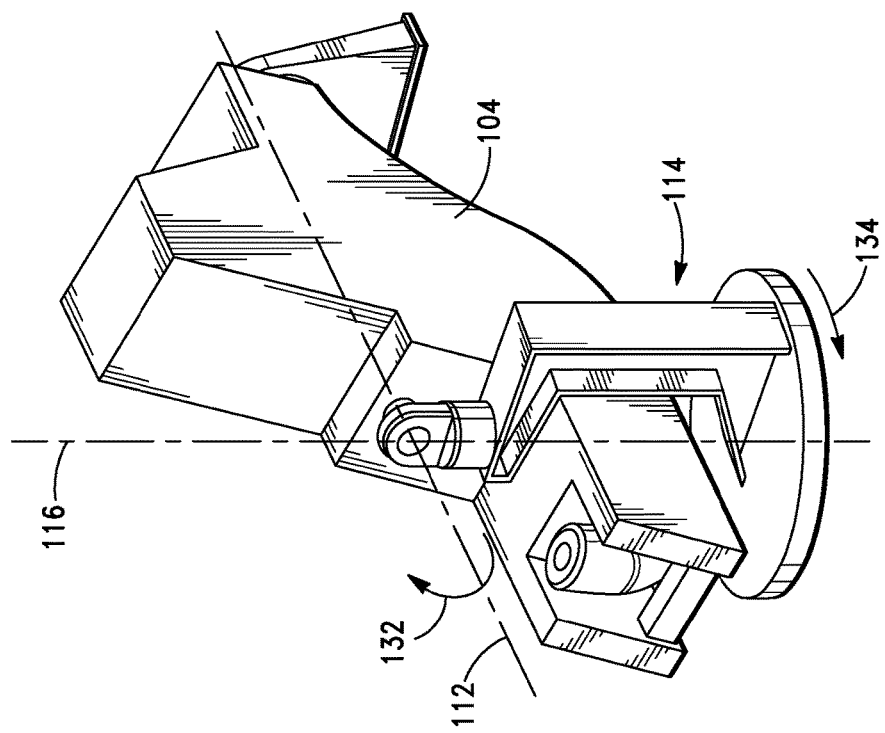

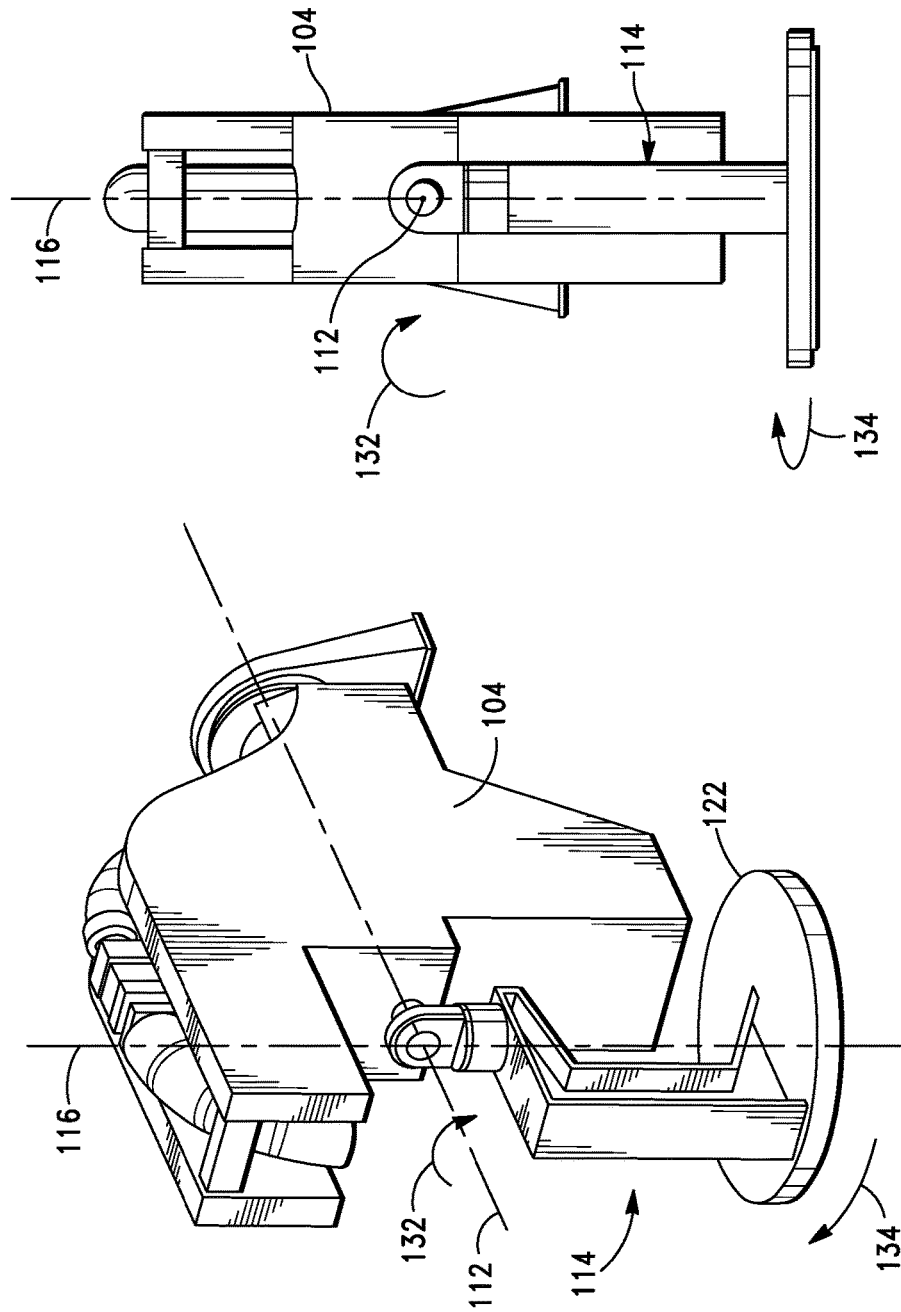

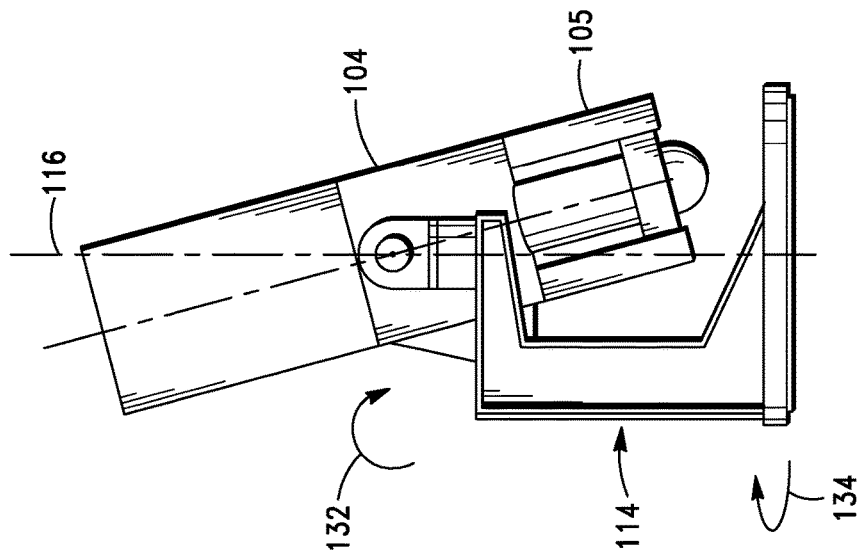
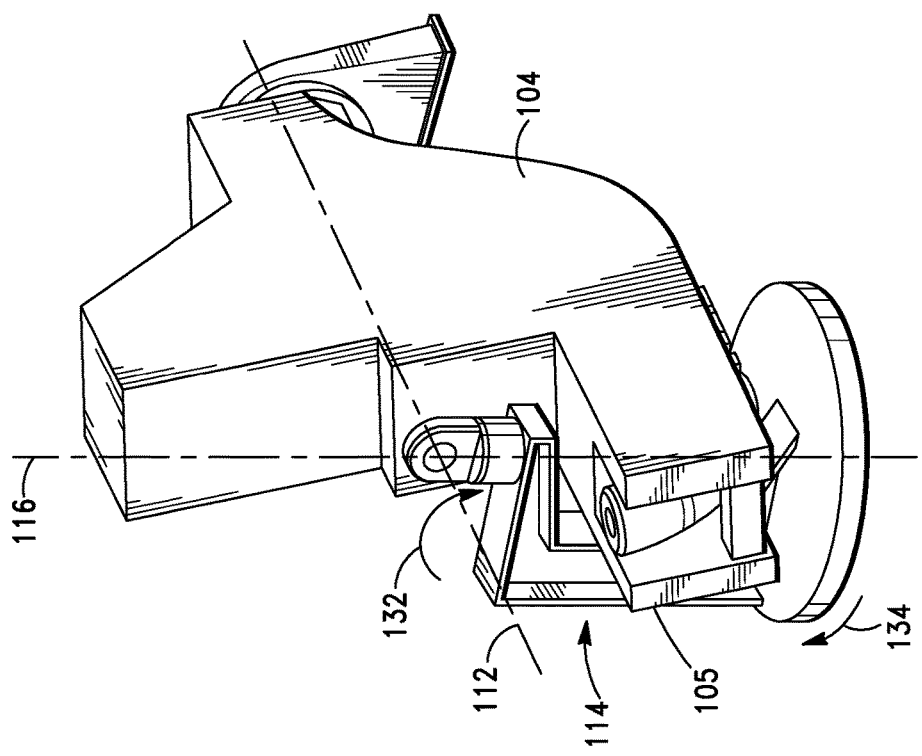
FIG. 7A
FIG. 7B

GANTRY SYSTEM FOR PARTICLE BEAM THERAPY

BACKGROUND

Embodiments of this disclosure relate generally to radiation systems and methods. In particular, various embodiments of a gantry system and a particle therapy system comprising such gantry system are described.

Particle therapy systems for treating patients are known. In particle therapy, charged particles such as protons or heavy ions are used to irradiate a region of interest such as tumor. Because of the "Bragg peak" effect, charged particles release most of their energy around the area where they stop. Therefore, by controlling the energy of charged particles, healthy tissue or critical organs distal to the source of charged particles receives substantially no radiation and the healthy tissue proximal to the source receives a significantly reduced amount of radiation. Furthermore, by choosing the energy of charged particles for irradiating different "layers" or "depths" of the tumor volume, the radiation dose distribution can be tailored to the shape of the tumor in all three dimensions.

A particle therapy system comprises an accelerator for producing particle beams, a beam transport line for transporting particle beams, and a beam delivery system located in a treatment room. The beam delivery system comprises a beam delivery line supported by a gantry body, which may rotate about the patient to allow particle beams to aim at the tumor from various angles. Conventional rotating gantries for particle therapy systems comprise custom made ring gantries. While conventional ring gantries can provide 360 or more degrees of rotation angles, most of them are huge and considerably expensive to build. Ring gantries are also difficult to align and very often show axial movement during rotation. Further, conventional ring gantries define a very limited space around the isocenter for the patient and healthcare personnel.

Arm gantries for proton therapy systems are currently available. FIGS. 1A and 1B illustrate a conventional proton beam delivery system 1 comprising a gantry body 2 generally in an L-shape supporting a beam delivery line 3 and a series of magnets 4 for bending and focusing the beam. The gantry body 2, supported by a front support bearing 5 and a rear support bearing 6, operates to rotate the beam delivery line 3 about a horizontal axis 7, allowing particle beams to aim at the tumor from various angles, as shown by the rotating gantry body 2 in phantom lines. One of the drawbacks of the conventional proton beam delivery system design is that the rotation angle of the gantry body 2 is limited. Because the supporting structure 8 supporting the front bearings 5 is fixedly mounted to the floor and wall, the gantry body 2 cannot rotate in full 360°. The gantry rotation angle (theta, FIG. 1B) is below 360°, usually between 200 and 220°.

SUMMARY

The disclosure provides a novel particle beam delivery system that overcomes these and other drawbacks of conventional beam delivery systems.

A particle beam delivery system of the disclosure comprises a beam delivery line of charged particles and a gantry body supporting the beam delivery line. The gantry body is rotatably supported by a first support and a second support. The gantry body serves to rotate the beam delivery line about a horizontal axis passing through the first and second support elements. The gantry body comprises a cantilevered portion configured to support at least a section of the beam delivery line in a cantilevered manner extended beyond the first and second support elements. The second support is supported by a structure which is rotatable about a vertical axis passing through the second support, thereby providing clearance for the cantilevered portion of the gantry body when rotating about the horizontal axis. The gantry body may be rotatable about the horizontal axis in 360 or more degrees, clockwise and/or counterclockwise.

The structure may be rotatable about the vertical axis in synchrony with rotation of the gantry body about the horizontal axis. For example, the structure is rotatable about the vertical axis clockwise when the gantry body rotates about the horizontal axis clockwise, and/or the structure is rotatable about the vertical axis counterclockwise when the gantry body rotates about the horizontal axis counterclockwise.

In an exemplary embodiment, the structure supporting the second support comprises a vertical arm and a horizontal arm, wherein the second support is supported at a cantilevered end portion of the horizontal arm, allowing the cantilevered portion of the gantry body to be accommodated in the space between the vertical and horizontal arms when the gantry body rotates to a location. The structure is generally C-shaped or U-shaped. In some embodiments, the distance from the vertical arm of the structure to the vertical axis is smaller than the distance from the outer edge of the cantilevered portion of the gantry body to the vertical axis.

A radiation system of the disclosure comprises an accelerator operable to produce a particle beam, a beam transport line coupled to the accelerator configured to transport the particle beam, and a beam delivery system operable to delivery the particle beam to a target volume. The accelerator may be operable to produce protons or heavy ions. The beam delivery system comprises a beam delivery line rotatably coupled to the beam transport line and a gantry body carrying the beam delivery line. The gantry body is rotatably supported by a first support and a second support. The gantry body serves to rotate the beam delivery line about a horizontal axis passing through the first and second supports. The gantry body comprises a cantilevered portion configured to support at least a section of the beam delivery line in a cantilevered manner extended beyond the first and second support elements. The second support is supported by a structure which is rotatable about a vertical axis passing through the second support, thereby providing clearance for the cantilevered portion of the gantry body when rotating about the horizontal axis. The gantry body may be rotatable about the horizontal axis in 360 or more degrees, clockwise and/or counterclockwise.

In some embodiments, the gantry body is rotatable about the horizontal axis in 360 or more degrees clockwise and/or counterclockwise. The structure is rotatable about the vertical axis simultaneously or in synchrony with the rotation of the gantry body about the horizontal axis.

In an exemplary embodiment, the structure may comprise a vertical arm and a horizontal arm, wherein the second support may be supported at a cantilevered end portion of the horizontal arm, thereby allowing the cantilevered portion of the gantry body to be accommodated in the space between the vertical and horizontal arms when the gantry is rotated to a location. The structure may be generally C-shaped or U-shaped.

The structure may be rotatable about the vertical axis clockwise when the gantry body rotates about the horizontal axis clockwise, and/or the structure may be rotatable about the vertical axis counterclockwise when the gantry body rotates about the horizontal axis counterclockwise.

A gantry assembly for supporting a radiation source is provided. The gantry assembly comprises a first support, a second support, and a gantry body rotatably supported by the first and second supports. The gantry body is configured to carry a radiation source and comprises a cantilevered portion configured to support the radiation source in a cantilevered manner extended beyond the first and second supports. The gantry is operable to rotate the radiation source about a horizontal axis passing through the first and second supports. The gantry assembly further comprises a structure supporting the second support. The structure is rotatable about a vertical axis passing through the second support, thereby providing clearance for the cantilevered portion of the gantry body when rotating about the horizontal axis. The gantry body may be rotatable about the horizontal axis in 360 or more degrees clockwise and/or counterclockwise.

The structure may be rotatable about the vertical axis simultaneously or in synchrony with rotation of the gantry body about the horizontal axis. For example, the structure may be rotatable about the vertical axis clockwise when the gantry body rotates about the horizontal axis clockwise, and/or the structure may be rotatable about the vertical axis counterclockwise when the gantry body rotates about the horizontal axis counterclockwise.

The structure may comprise a vertical arm and a horizontal arm. The second support element may be supported at a cantilevered end portion of the horizontal arm, thereby allowing the cantilevered portion of the gantry body to be accommodated in the space between the vertical and horizontal arms when the gantry body is rotated to a location. The structure may be C-shaped or U-shaped. In an embodiment, the distance between the vertical arm of the structure to the vertical axis may be smaller than the distance between the outer edge of the cantilevered portion of the gantry to the vertical axis.

This Summary is provided to introduce selected embodiments in a simplified form and is not intended to identify key features or essential characteristics of the claimed subject matter, nor is it intended to be used as an aid in determining the scope of the claimed subject matter. The selected embodiments are presented merely to provide the reader with a brief summary of certain forms the invention might take and are not intended to limit the scope of the invention. Other aspects and embodiments of the disclosure are described in the section of Detailed Description.

BRIEF DESCRIPTION OF THE DRAWINGS

These and various other features and advantages will become better understood upon reading of the following detailed description in conjunction with the accompanying drawings and the appended claims provided below, where:

FIG. 2 is a block diagram illustrating a particle therapy system according to embodiments of the disclosure;

FIGS. 4A and 4B illustrate an about 180-190 degree rotation of the particle beam delivery system of FIGS. 3A-3B, counterclockwise from a gantry angle of 0 degree to a gantry angle of about −180 to −190 degree; and FIGS. 5A-5B, 6A-6B, and 7A-7B illustrate an about 360-degree rotation of the particle beam delivery system of FIGS. 3A-3B, clockwise from a gantry angle of about −180 to −190 degree to a gantry angle of about +180 to +190 degree.

DETAILED DESCRIPTION

Figure 1B:
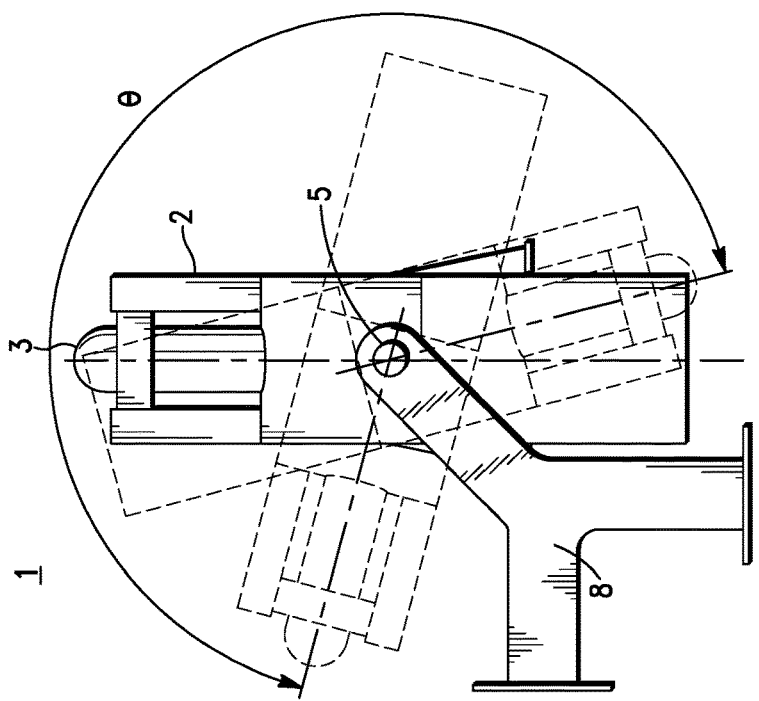
FIGS. 1A and 1B illustrate a conventional proton beam delivery system.
Figure 1A:
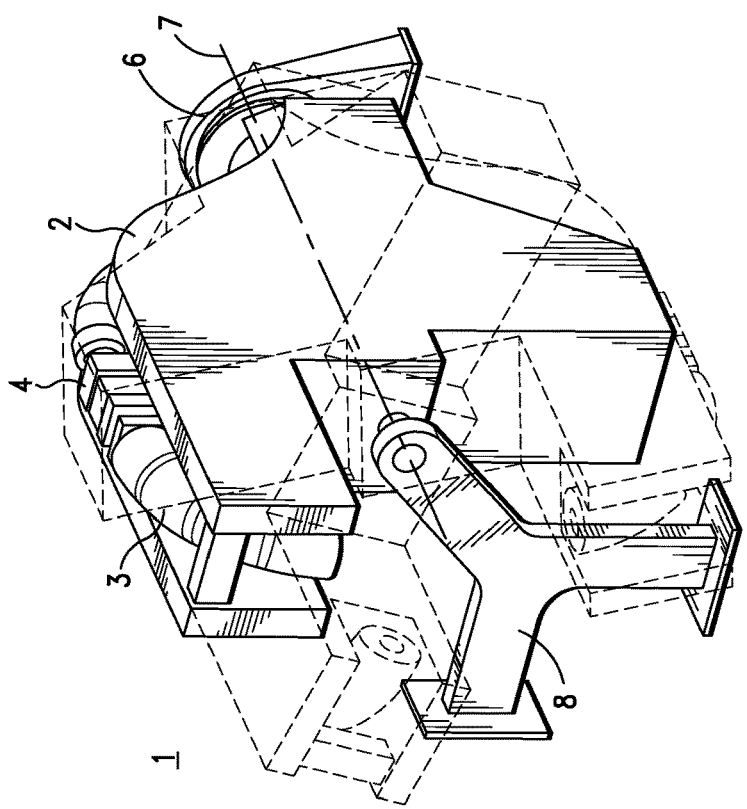

Various embodiments of a radiation system are described. It is to be understood that the disclosure is not limited to the particular embodiments described. An aspect described in conjunction with a particular embodiment is not necessarily limited to that embodiment and can be practiced in any other embodiments. For instance, while various embodiments are described in connection with a particle therapy system, it will be appreciated that the invention can also be practiced in other radiation apparatuses and modalities such as radiotherapy and/or imaging systems using x-rays.

Various embodiments are described with reference to the figures. It should be noted that some figures are not necessarily drawn to scale. The figures are only intended to facilitate the description of specific embodiments, and are not intended as an exhaustive description or as a limitation on the scope of the disclosure. Further, in the figures and description, specific details may be set forth in order to provide a thorough understanding of the disclosure. It will be apparent to one of ordinary skill in the art that some of these specific details may not be employed to practice embodiments of the disclosure. In other instances, well known components or process steps may not be shown or described in detail in order to avoid unnecessarily obscuring embodiments of the disclosure.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise. The term "first" or "second" etc. may be used to distinguish one element from another. The use of the term "first" or "second" should not be construed as in any particular order unless the context clearly dictates otherwise. Further, the singular form of "first" and "second" include plural references unless the context clearly dictates otherwise.

As used herein, the term "particle beam" refers to a beam of charged particles such as protons or heavy ions such as ions of helium, carbon, neon, argon, or other charged elemental particles.

As used herein, the term "radiation source" refers to a source of radiation such as electrons, x-rays, or charged particles such as protons or heavy ions such as ions of helium, carbon, neon, argon, or other charged elemental particles. The radiation source may be a source of therapeutic radiation or a source of radiation suitable for imaging.

Referring to FIG. 2, a radiation system 10 according to embodiments of the disclosure will now be described. As shown, the exemplary radiation system 10 includes an accelerator 12, a beam transport line 14, and a beam delivery system 16. A subject 18, e.g., a patient to be treated, is positioned on a patient support 20. Control 22 controls the operation of the accelerator 12, beam transport line 14, beam delivery system 16, and patient support 20.

The accelerator 12 may include a source of charged particles such as protons or heavy ions such as ions of helium, carbon, neon, argon, or other charged elemental particles. The accelerator 12 may include a cyclotron, synchrotron, linear accelerator, or any other accelerators configured to accelerate charged particles. The energy of the charged particles may be greater than 20, 50, 70, 100, 250 or 500 MeV depending on specific applications.

The beam transport line 14 transports a beam of charged particles from the accelerator 12 to the beam delivery system 16 typically located in a treatment room different from that of the accelerator 12. For clarity of illustration and description, a single beam delivery system 14 is shown. It should be noted that the radiation system 10 may include two or more beam delivery systems located in different treatment rooms and thus two or more beam transport lines used to transport charged particles from the accelerator 12 to two or more treatment rooms. Bending magnets (not shown) may be used to steer the particle beam from the accelerator 12 to the beam delivery system 16. The beam transport line 14 may include energy modification components (not shown) such as energy degraders for modifying the energy of particles extracted from the accelerator 12, slits for adjusting the intensity of particles from the accelerator 12. The beam transport line 14 may be fixed or stationary.

The beam delivery system 16 operates to deliver a beam of particles to a target volume in the patient 18. The beam delivery system 16 is rotatable about an axis e.g. a horizontal axis 19, to allow particle beams to be delivered to the target volume from various angles. The beam delivery system 16 may include a beam delivery line 22 and a gantry body 24 carrying or supporting the beam delivery line 22. The beam delivery line 22 is coupled to the beam transport line 14 at an end for receiving a beam of particles. The beam delivery line 22 may be rotatable relative to the beam transport line 14 via a joint 15. The gantry body 24 carries or supports the beam delivery line 22 and is rotatable about a horizontal axis 19 to allow the particle beam to aim at a target volume in the patient 18 from various angles.

The beam delivery system 16 may include a nozzle (not shown) coupled to the beam delivery line 22, inside of which may include various devices or components for modulating and monitoring the particle beam. Depending on applications, the nozzle may include energy modifiers, beam scattering media, scanning magnets, beam monitors, collimators, compensators, or other components configured to modulate the particle beam. By way of example, the nozzle may include scanning magnets e.g. vertical and/or horizontal scanning magnets for fast scanning a pencil beam over a target volume. A pencil beam may be continuously moved along predetermined scan-lines over a target (raster scan). Alternatively, a pencil beam may be switched off and on in a predetermined time interval when moving from one spot to another (spot scanning). The intensity of the beam can be controlled to ensure each target spot receives a desired dose. In the case of raster scanning, the velocity of the pencil beam may be adjusted to the desired dose. In the case of spot scanning, the spot dwelling time may be adjusted to the desired dose. The intensity of the pencil beam may be controlled or adjusted by controlling the particle accelerator and/or the slits disposed along the bean path. The particle beam may scan (either raster scan or spot scan) over the whole area of a slice of the target volume. The energy of the beam may be selected such that the Bragg peaks of the scan are deposited on the slice. By modulating the energy of the beam, the whole volume of the target can be uniformly irradiated layer by layer. In some applications, the nozzle may include single or double scatterers in combination with other components to provide a broad uniform modulated particle beam. In some applications, the nozzle may include wobbling magnets to provide a broad, uniform particle beam profile.

Using the beam delivery system 16, the charged particles for a treatment fraction may be delivered to a target volume with one single rotation or multiple rotations. The rotation may be a complete rotation in about 360 degrees or a partial rotation in any degree less than 360 degrees such as 45, 90, 180, 270, or 330 degrees, for example. The rotation of the beam delivery system 16 may be continuous during which the charged particles are delivered to the target. Alternatively, the rotation may be non-continuous or may operate in an alternating mode of rotation, stop, and rotation. Charged particles may be delivered to a target when the beam delivery system 16 rotates, or when the beam delivery system 16 is stationary. For example, the delivery of charged particles for a treatment fraction may be carried out at discrete or selected angles during partial or complete rotation. One or more of the parameters of the charged particles including the energy, the intensity, the beam direction, or the beam shape may be modulated or concurrently modulated during the rotation or pause of the beam delivery system 16.

Figure 3A:
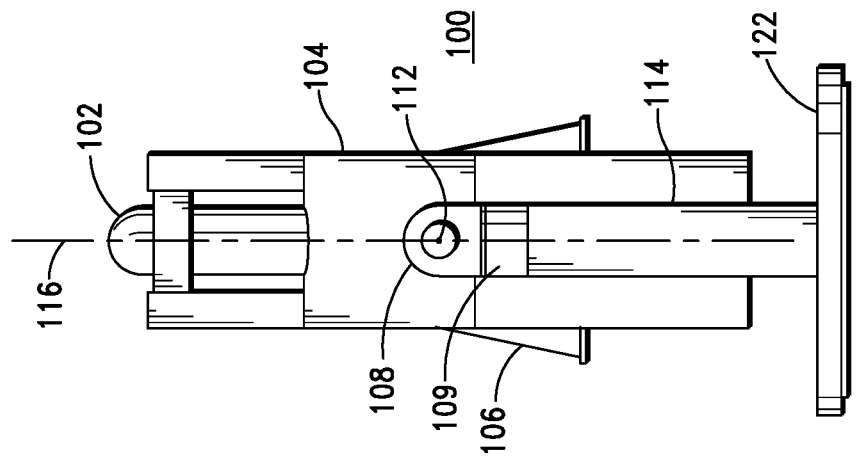
FIGS. 3A and 3B illustrate a particle beam delivery system according to embodiments of the disclosure.
Figure 3B:
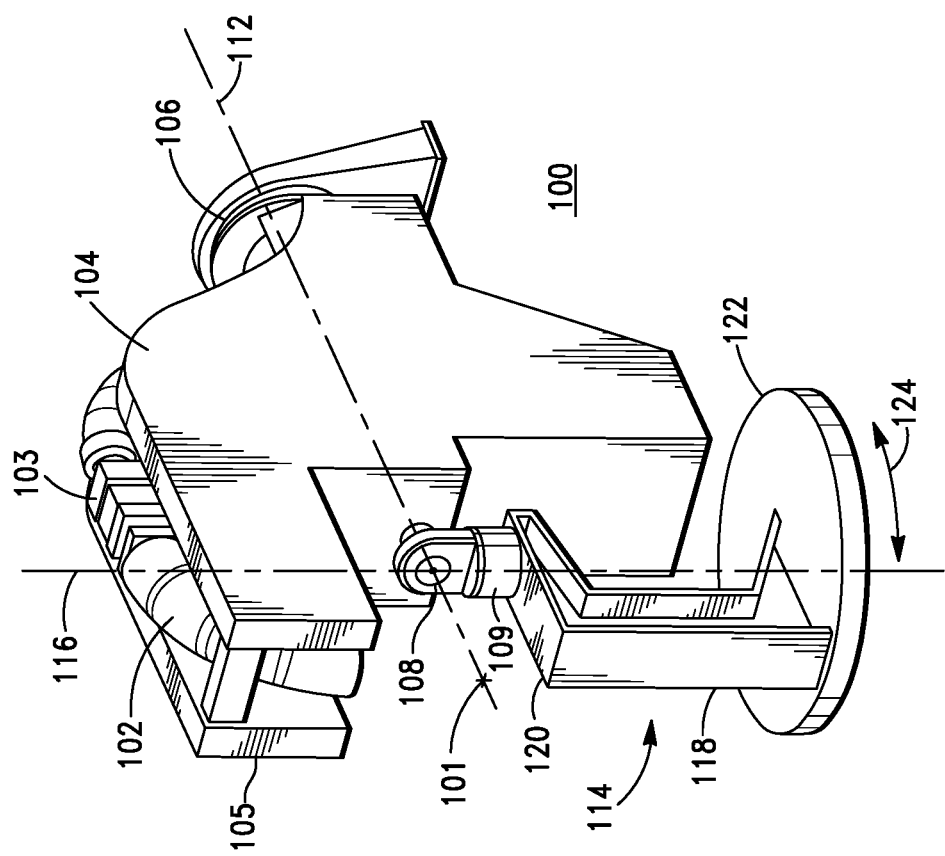

FIGS. 3A and 3B illustrate an exemplary beam delivery system 100 according to embodiments of the disclosure. As shown, the beam delivery system 100 comprises a beam delivery line 102 of charged particles and a gantry body 104 carrying or supporting the beam delivery line 102. The gantry body 104 is rotatably supported by a first support 106 and a second support 108. The gantry body 104 is rotatable about a horizontal axis 112 passing through the first and second supports 106 and 108, allowing the beam delivery line 102 supported by the gantry body 104 to rotate about the horizontal axis 112. A column or structure 114 supports the second support 108. According to embodiments of the disclosure, the structure 114 is rotatable about a vertical axis 116 passing through the second support 108, thereby providing clearance for the gantry body 104 when rotating about the horizontal axis 112.

The gantry body 104 serves to support the beam delivery line 102, which may be very heavy and typically weigh in tons. The gantry body 104 holds the beam delivery line 102 in place during rotation around the patient. The gantry body 104 may be configured or shaped according to the configuration or arrangement of the beam delivery line 102. By way of example, the beam delivery line 102 may include a first end section coupled to the beam transport line, therefore may include a generally horizontal section in line with the beam transport line. The beam delivery line 102 may include a second end section coupled to a nozzle device (not shown), which allows the beam to aim at the target volume at angles generally perpendicular to the horizontal line 112. The beam delivery line 102 may include a third curved section connecting the first and second end sections. The gantry body 104 may be structured or configured to have sections generally conforming to the arrangement or configuration of the sections of the beam delivery line 102. Various magnets 103 may be used to bend and/or focus the particle beam from the first end section to the second end section of the beam delivery line 102.

In accordance with embodiments of the disclosure, the gantry body 104 may include a cantilevered portion 105 configured to support at least a section of the beam delivery line 102 in a cantilevered manner extended beyond the second support element 108. The cantilevered portion 105 of the gantry body 104 allows a section of the beam delivery line 102 and thus the nozzle device to be supported in a cantilevered manner, thereby providing free or open space around the axis of rotation 112 for patient positioning and for healthcare personnel to access to the patient. By way of example, the distance between the isocenter 101 of the beam delivery system 100 and second support element 108 may be about 1000 mm.

The rotation of the gantry body 104 can be actuated by a motor (not shown) such as an electric motor, hydraulic motor, and/or other suitable mechanisms. The first and second supports 106, 108 may each comprise a bearing, allowing the gantry body 104 to rotate about the horizontal axis 112. To compensate the heavy weight of the beam delivery line 102 and various magnets 103, a counterweight (not shown) may be included in the gantry body 104, disposed generally opposite to the beam delivery line 102 with respect to the axis of rotation 112.

The second support 108 may be supported by a column or structure 114. In accordance with embodiments of the disclosure, the structure 114 can rotate about a vertical axis 116 passing through the second support 108, providing clearance for the gantry body 104 and/or the cantilevered portion 107 of the gantry body 104, which otherwise would be obstructed if the structure 114 is non-rotatable or fixed when the gantry body 104 is rotating about the horizontal axis 124.

The structure 114 may be rotatable about the vertical axis 116 simultaneously or in synchrony with the rotation of the gantry body 104 about the horizontal axis 112. For example, the structure 114 may be rotatable about the vertical axis 116 clockwise when the gantry body 104 rotates about the horizontal axis 112 clockwise. Alternatively or in addition, the structure 114 may be rotatable about the vertical axis 116 counterclockwise when the gantry body 104 rotates about the horizontal axis 112 counterclockwise.

The structure 114 may be constructed sufficiently stiff and strong to carry or support the weight of the gantry body 104 and the beam delivery line 102. The structure 114 may be constructed using I-beams, box-beams or any other suitable frames or beams. An exemplary structure 114 shown in FIGS. 3A-3B comprises a vertical arm 118 and a horizontal arm 120. At a cantilevered end portion of the horizontal arm 120, the second support element 108 can be supported. The space between the horizontal arm 120 and vertical arm 118 allows the cantilevered portion 105 of the gantry body 104 to be accommodated when the gantry body 104 is rotating to a location. As shown, the structure 114 may be U-shaped or C-shaped. It should be noted that the structure 114 can be in any other suitable shape as long as space is provided to accommodate the cantilevered portion 105 of the gantry body 104 when rotating to a location.

The structure 114 may be mounted to a rotating base member 122. The base member 122 may be a driven by a drive system (not shown) to allow it to rotate clockwise and/or counterclockwise as indicated by arrow 124, thereby allowing the structure 114 to rotate about the vertical axis 116 clockwise and/or counterclockwise. A bearing such as a slew bearing 109 may be used to decouple the rotation of the structure 114 about the vertical axis 116 from the rotation of the gantry body 104 about the horizontal axis 112.

The configuration of the structure 114 and the capability of rotation of the structure 114 provides clearance and/or accommodates the cantilevered portion 105 of the gantry body 104 when the gantry body 104 rotates, thereby allowing the gantry body 104 to rotate about the horizontal axis 112 in 360 or more degrees clockwise and/or counterclockwise without obstruction. Further, the capability of rotation of the structure 114 allows the vertical arm 118 of the structure 114 to be closer to the rotating gantry 104. As such, the possibility of misalignment of the beam delivery system 100 due to the deformation of the horizontal arm 120 is reduced or minimized. According to embodiments of the disclosure, the distance between the vertical arm 118 of the structure 114 and the vertical axis 116 may be equal to or smaller than the distance between the outer edge of the cantilevered portion 105 of the gantry body 104 and the vertical axis 116. Alternatively, the distance between the vertical arm 118 of the structure 114 and the vertical axis 116 may be equal to or smaller than the distance between the isocenter 101 and the vertical axis 116.

FIGS. 4A and 4B illustrate an embodiment where the structure 114 rotates simultaneously or in synchrony with the rotation of the gantry body 104 in operation. From a gantry angle of 0 degree (FIGS. 3A-3B), the gantry body 104 may rotate about the horizontal axis 112, e.g. counterclockwise, as indicated by arrow 128 shown in FIGS. 4A and 4B. Simultaneously or in synchrony with the rotation of the gantry body 104, the structure 114 may rotate about the vertical axis 116, e.g. counterclockwise, as indicated by arrow 130 shown in FIGS. 4A and 4B. As the structure 114 rotates about the vertical axis 116, the angle of the horizontal arm 120 with respect to the horizontal axis 112 changes, or the vertical arm 118 changes its location. For example, when the gantry body 104 rotates counterclockwise to a location approaching to −180 degree as shown in FIGS. 4A-4B, the structure 114 rotates to a location where the horizontal arm 120 of the structure 114 is approaching 90 degree with respect to the horizontal axis 112. The cantilevered portion 105 of the gantry body 104, which otherwise would be obstructed by the vertical arm 118 if the structure 114 does not move, can be now accommodated in the space between the vertical arm 118 and the horizontal arm 120 of the structure 114.

FIGS. 5A-5B through FIGS. 7A-7B illustrate that the structure 114 of the disclosure allows the gantry body 104 to rotate 360 or more degrees. From a gantry angle of about −180 or −190 degree shown in FIGS. 5A-5B, the gantry body 104 can rotate about the horizontal axis 112 clockwise, as indicated by arrow 132. Simultaneously or in synchrony with the rotation of the gantry body 104, the structure 114 also rotates about the vertical axis 116, clockwise, as indicated by arrow 134. This simultaneous rotation of the gantry body 104 and the structure 114 allow the gantry body 104 and the structure 114 return to locations where the gantry body 104 has a gantry angle of 0 degree and the horizontal arm 120 of the structure 114 is in line of with the horizontal axis of rotation 112, as shown in FIGS. 6A-6B.

Referring to FIGS. 6A-6B, the gantry body 104 may continue to rotate about the horizontal axis 112 clockwise as indicated by arrow 132, to a gantry angle approaching to +180 or +190 degrees, as shown in FIGS. 7A-7B. Simultaneously or in synchrony with the rotation of the gantry body 104, the structure 114 may also continue to rotate about the vertical axis 116 clockwise as indicated by arrow 134, changing the angle of the horizontal arm 120 of the structure 114 to about 90 degree with respect to the horizontal axis 112, or changing the location of the vertical arm 118 of the structure 114. The cantilevered portion 105 of the gantry body 104, which otherwise would be obstructed by the vertical arm 118 if the structure 114 does not move, can be now accommodated in the space between the vertical arm 118 and the horizontal arm 120 of the structure 114 in a new location, as shown in FIGS. 7A-7B.

Embodiments of a radiation system have been described. Those skilled in the art will appreciate that various other modifications may be made within the spirit and scope of the invention. For example, while various embodiments of a gantry body are described in connection with a particle therapy system, it will be appreciated that the gantry body can be used to carry or support a radiation source producing x-rays for treatment or imaging. All these or other variations and modifications are contemplated by the inventors and within the scope of the invention.

What is claimed is:

1. A particle beam delivery system, comprising:
   a beam delivery line of charged particles;
   a gantry body supporting the beam delivery line of charged particles;
   a first support and a second support rotatably supporting the gantry body, the gantry body being rotatable about a horizontal axis passing through the first and second supports; and
   a structure supporting the second support, wherein
   the gantry body comprises a cantilevered portion configured to support at least a section of the beam delivery line in a cantilevered manner extended beyond the first and second supports; and
   the structure is rotatable about a vertical axis passing through the second support, thereby providing clearance for the cantilevered portion of the gantry body when rotating about the horizontal axis.

2. The particle beam delivery system of claim 1, wherein the structure is rotatable about the vertical axis in synchrony with rotation of the gantry body about the horizontal axis.

3. The particle beam delivery system of claim 2, wherein the structure is rotatable about the vertical axis clockwise when the gantry body rotates about the horizontal axis clockwise, and/or the structure is rotatable about the vertical axis counterclockwise when the gantry body rotates about the horizontal axis counterclockwise.

4. The particle beam delivery system of claim 2, wherein the gantry body is rotatable about the horizontal axis in 360 degrees clockwise and/or counterclockwise.

5. The particle beam delivery system of claim 1, wherein the structure comprises a vertical arm and a horizontal arm, wherein the second support is supported at a cantilevered end portion of the horizontal arm, thereby allowing the cantilevered portion of the gantry body to be accommodated in space between the vertical and horizontal arms when the gantry body is rotated to a location.

6. The particle beam delivery system of claim 5, wherein the structure is generally C-shaped or U-shaped.

7. The particle beam delivery system of claim 5, wherein the structure is rotatable about the vertical axis clockwise when the gantry body rotates about the horizontal axis clockwise, and/or the structure is rotatable about the vertical axis counterclockwise when the gantry body rotates about the horizontal axis counterclockwise.

8. The particle beam delivery system of claim 5, wherein the gantry body is rotatable about the horizontal axis in 360 or more degrees clockwise and/or counterclockwise.

9. The particle beam delivery system of claim 5, wherein a distance from the vertical arm of the structure to the vertical axis is smaller than a distance from an edge of the cantilevered portion of the gantry body to the vertical axis.

10. A radiation system, comprising:
    an accelerator operable to produce a particle beam;
    a beam transport line coupled to the accelerator configured to transport the particle beam; and
    a beam delivery system operable to deliver the particle beam to a target volume, wherein the beam delivery system comprises:
    a beam delivery line rotatably coupled to the beam transport line;
    a gantry body carrying the beam delivery line;
    a first support and a second support rotatably supporting the gantry body, allowing the gantry body carrying the beam delivery line to rotate about a horizontal axis passing through the first and second supports; and
    a structure supporting the second support, wherein the gantry body comprises a cantilevered portion configured to support at least a section of the beam delivery line in a cantilevered manner extended beyond the first and second supports, the structure is rotatable about a vertical axis passing through the second support, thereby providing clearance for the cantilevered portion of the gantry body when rotating about the horizontal axis.

11. The radiation system of claim 10, wherein the accelerator is operable to produce protons or heavy ions.

12. The radiation system of claim 10, wherein the gantry body is rotatable about the horizontal axis in 360 or more degrees clockwise and/or counterclockwise.

13. The radiation system of claim 10, wherein the structure is rotatable about the vertical axis simultaneously with rotation of the gantry body about the horizontal axis.

14. The radiation system of claim 10, wherein the structure comprises a vertical arm and a horizontal arm, wherein the second support is supported at a cantilevered end portion of the horizontal arm, thereby allowing the cantilevered portion of the gantry body to be accommodated in space between the vertical and horizontal arms when the gantry rotates to a location.

15. The radiation system of claim 14, wherein the structure is generally C-shaped or U-shaped.

16. The radiation system of claim 14, wherein the structure is rotatable about the vertical axis clockwise when the gantry body rotates about the horizontal axis clockwise, and/or the structure is rotatable about the vertical axis counterclockwise when the gantry body rotates about the horizontal axis counterclockwise.

17. The radiation system of claim 10, wherein a distance from the vertical arm of the structure to the vertical axis is smaller than a distance from an edge of the cantilevered portion of the gantry body to the vertical axis.

18. A gantry system, comprising:
    a first support;
    a second support;
    a gantry body rotatably supported by the first and second supports, the gantry body being configured to carry a radiation source and comprising a cantilevered portion configured to support the radiation source in a cantilevered manner extended beyond the first and second supports, wherein the gantry is operable to rotate the radiation source about a horizontal axis passing through the first and second supports; and
    a structure supporting the second support, wherein the structure is rotatable about a vertical axis passing through the second support, thereby providing clearance for the cantilevered portion of the gantry body when rotating about the horizontal axis.

19. The gantry system of claim 18, wherein the structure is rotatable about the vertical axis in synchrony with rotation of the gantry body about the horizontal axis.

20. The gantry system of claim 19, wherein the structure is rotatable about the vertical axis clockwise when the gantry body rotates about the horizontal axis clockwise, and/or the structure is rotatable about the vertical axis counterclockwise when the gantry body rotates about the horizontal axis counterclockwise.

21. The gantry system of claim 19, wherein the gantry body is rotatable about the horizontal axis in 360 or more degrees clockwise and/or counterclockwise.

22. The gantry system of claim 18, wherein the structure comprises a vertical arm and a horizontal arm extended from an end of the vertical arm, wherein the second support is supported at a cantilevered end portion of the horizontal arm, thereby allowing the cantilevered portion of the gantry body to be accommodated in space between the vertical and horizontal arms when the gantry body is rotated to a location.

23. The gantry system of claim 22, wherein the structure is generally C-shaped or U-shaped.

24. The gantry system of claim 22, wherein the structure is rotatable about the vertical axis clockwise when the gantry body rotates about the horizontal axis clockwise, and/or the structure is rotatable about the vertical axis counterclockwise when the gantry body rotates about the horizontal axis counterclockwise.

25. The gantry system of claim 22, wherein the gantry body is rotatable about the horizontal axis in 360 or more degrees clockwise and/or counterclockwise.

26. The particle beam delivery system of claim 22, wherein a distance from the vertical arm of the structure to the vertical axis is smaller than a distance from an edge of the cantilevered portion of the gantry to the vertical axis.

* * * * *